United States Patent [19]

Holler

[11] Patent Number: 5,532,141
[45] Date of Patent: Jul. 2, 1996

[54] PROCESS FOR OBTAINING GANGLIOSIDE LIPIDS

[76] Inventor: Larry D. Holler, South Dakota State University, Brookings, S. Dak. 57007

[21] Appl. No.: 489,804

[22] Filed: Jun. 13, 1995

[51] Int. Cl.[6] .................... C12P 19/26; C12P 19/44; C08B 37/00; C07G 3/00
[52] U.S. Cl. .................... 435/74; 424/520; 424/570; 435/84; 435/101; 435/105; 435/134; 514/25; 514/61; 530/424; 530/359; 536/18.5; 536/55.3; 536/127; 554/193; 554/207; 554/210
[58] Field of Search ................ 424/570, 520; 514/25, 61; 435/74, 134, 84, 105, 101; 536/18.5, 127, 55.3; 530/424, 359; 554/207, 210, 193

[56] References Cited

U.S. PATENT DOCUMENTS

| | | | |
|---|---|---|---|
| 4,471,057 | 9/1984 | Koprowski et al. | 436/518 |
| 4,521,593 | 6/1985 | Martin | 536/55.3 |
| 4,710,490 | 12/1987 | Catsimpoouas et al. | 514/25 |
| 4,771,039 | 9/1988 | Tanaka et al. | 514/25 |
| 4,778,787 | 10/1988 | Catsimpoouas et al. | 514/25 |
| 4,868,292 | 9/1989 | Yokoyama et al. | 536/18.5 |
| 4,888,324 | 12/1989 | Catsimpoouas et al. | 514/25 |
| 5,006,470 | 4/1991 | Yamaguchi et al. | 435/240.27 |
| 5,077,202 | 12/1991 | Seto et al. | 435/257.3 |
| 5,112,956 | 5/1992 | Tang et al. | 530/424 |
| 5,272,138 | 12/1993 | Hakomori et al. | 514/61 |
| 5,275,939 | 1/1994 | Sugimori et al. | 435/84 |
| 5,284,941 | 2/1994 | Colarow | 536/127 |
| 5,296,360 | 3/1994 | Sugimori et al. | 435/101 |
| 5,466,782 | 11/1995 | Rousset | 536/18.5 |
| 5,472,969 | 12/1995 | Platt et al. | 514/314 |
| 5,484,596 | 1/1996 | Hanna et al. | 424/277.1 |
| 5,484,611 | 1/1996 | Noble et al. | 424/570 |

*Primary Examiner*—Herbert J. Lilling
*Attorney, Agent, or Firm*—Felfe & Lynch

[57] ABSTRACT

A method is taught whereby improved yields of lipid containing molecules, such as gangliosides, are obtained. Involved is the treatment of neural tissue from animals afflicted with GM1 gangliosidosis. Only members of the ovine family, e.g., sheep are so treated.

10 Claims, No Drawings

PROCESS FOR OBTAINING GANGLIOSIDE LIPIDS

FIELD OF THE INVENTION

This invention relates to the extraction of lipid containing molecules from natural materials. More particularly, it relates to the extraction of gangliosides from ovine tissue.

BACKGROUND AND PRIOR ART

While much of current biology focuses on proteins, and their uses, it must not be forgotten that other molecules are extremely important in a number of biological contents. Lipids, and lipid containing molecules (e.g. glycolipids), have an important role as pharmaceutical agents, immunogens, and so forth.

Exemplary of the important lipid containing molecules is the class of glycolipids referred to as gangliosides. Gangliosides belong to a family of glycolipids referred to as glycosphingolipids. These glycosphingolipids contain at least one neutral sugar residue at the polar head group of a lipid molecule. Gangliosides are molecules which contain at least one sialic acid residue in this oligosaccharide head. These sialic acid residues give the head, and the glycolipid molecule itself, a net negative charge. For a discussion of gangliosides, and of glycolipids and their structures in general, attention is drawn to the well known textbooks, Lehninger, *Biochemistry* (Worth Publishers, 1981), pp. 287–295, especially 294–295. This material is incorporated by reference in its entirety. Exemplary of the important role of gangliosides in a therapeutic context is Mahadnik et al., "Gangliosides In Treatment of Neural Injury and Disease", Drug Development Res. 15: 337–360 (1988). See also U.S. Pat. No. 4,710,490 to Catsimpoolas et al. (gangliosides and angiogenesis); Mynard et al, U.S. Pat. No. 4,347,244 (GM1 and diarrhea); Horowitz, "Ganglioside (Cronassial) Therapy in Diabetic Neuropathy", Adv. Exp. Med & Biol 174: 593,600 (1984); Karpiatz et al., "Exogenous Gangliosides Enhance Recovery from CNS Injury", Adv. Exp. Med. & Biol. 174: 489–497 (1984), all of which are incorporated by reference. The Catsimpoolas et al. patent is of special relevance in that it sets forth in great detail, flow charts summarizing various protocols for securing lipid containing molecules, while Catsimpoolas et al used mammalian omentum as a source for their gangliosides and lipids, other tissue sources may be used, as is elaborated infra.

Lipids, unlike proteins, are not coded for by genes. Thus, one desiring large amounts of lipid containing molecules does not have the resources afforded by recombinant genetics available to him or her. Securing large amounts of lipid containing material forces the investigator to confront the problems and pitfalls of natural product chemistry.

Most lipid containing materials are secured after a rich source of the lipid material of interest is identified, and an extraction protocol developed. Generally, this requires some treatment of the source material, followed by contact with a solvent. The lipid of interest is then separated from the solvent.

The methodology is never as simple as presented, however. To begin with, "rich source" is very misleading. For many lipid containing materials, there is no "rich source", as the total yield can range between nanograms and micrograms. Further, within a generic group of materials, variation from sample to sample should be expected. Also, extraction protocols, even in their most defined formats, are frequently very harsh on the target molecule or molecules. Frequently, there is a loss of product which can be attributed to the purification protocol itself. Another issue is the fact that many lipid molecules demonstrate extremely similar structures and properties in solution, so it is very difficult to resolve individual species following extraction.

The foregoing are simply exemplary of the problems in the field, and should not be taken to be comprehensive of all issues as faced by the artisan. Some headway has been made however, and this is the subject of the invention.

Veterinary medicine is aware of a condition referred to as ovine GM1 gangliosidosis, as reported by, e.g., Ahern-Riddel et al, Biochem. Genet. 26: 733–746 (1988); Ahern-Rindell et al, Somat, Cell & Molecular Genet. 15(6): 525–533 (1989); Murane, et al., Am. J. Pathol. 134:263–270 (1989); Prieur et al., J. Hered. 81: 245–249 (1988), Prieur et al., Am. J. Pathol. 139(6): 1511–1513 (1991); all of which are incorporated by reference in their entirety. The disease, which affects lambs, is characterized by a profound deficiency in acid $\beta$-galactosidase activity, and a partial deficiency in $\alpha$-neuraminidase activity. The condition does have a parallel in humans, i.e., human GM1 gangliosidosis, although the decrease in a neuraminidase levels has not been found in humans. Analysis of the neural tissue of lambs afflicted with GM1 gangliosidosis has revealed that these tissues contain surprising large amounts of lipid containing molecules, especially glycolipids such as gangliosides. The levels observed are several orders of magnitude greater than the vanishingly small amounts found in other tissue sources.

Hence, it is an object of the invention to provide a method for obtaining enhanced yields of lipid containing molecules, via extraction of neural tissue of animals, e.g., ovine animals, suffering from GM1 gangliosidosis.

How this, and other aspects of the invention are achieved will be seen from the disclosure which follows.

DETAILED DESCRIPTION OF PREFERRED EMBODIMENT

EXAMPLE 1

The experiments described herein used nine lambs, homozygous for GM1 gangliosidosis, and nine phenotypically normal lambs. The lambs were age matched, and generated from four successive lambing seasons. Genotypes of both affected (i.e., GM1 gangliosidosis), and normal lambs (controls) were determined via enzymatic analysis of either peripheral blood leukocytes ("PBLs"), or cultured dermal fibroblasts, obtained by skin biopsy as per Suzuki, in Glew, et al., ed *Practical Enzymology of the Sphingolipidoses* (pp. 102–136) (Alan R. Liss, N.Y. 1977) and modified by Ahern-Rindell, et al., Biochem. Genet. 26: 733–746 (1988). In the analysis, three affected, and three normal controls were evaluated at one day of age, 120 days of age, and 170 days of age (cerebral cortex analysis), while two affected and two control lambs were also assayed at these three time points.

Lambs were euthanized (intravenous injection of sodium pentobarbitol), brains were removed rapidly, hemisectioned, and half was stored at −70° C. until use Samples in all of the analyses which follow were taken from the materials prepared via the preceding protocol.

EXAMPLE 2

Samples of cerebral cortex rostral and caudal to the transverse sulcus, and cerebellar cortex from central vermis were used to prepare ganglioside fractions. Tissues were thawed, and homogenized (1.0 g, 2 ml water), twenty volumes of chloroform: methanol (C:M 1:1) were added to a final ratio of 10:10:1 (C:M:$H_2O$), to extract total lipids. The homogenates were stirred, continuously, for 12 hours, and supernatant was cleared, using centrifugation (1000xg), and then collected. Residues were extracted for four hours in 10 volumes of C:M(2:), after which supernatants were combined, and evaporated to dryness on a rotary evaporator. The residue was dissolved in 51 ml of C:M (2:1), and any phospholipids in the solute were hydrolyzed by adding 17 ml of 1MKOH (n $CH_3OH$), at room temperature for 12 hours. The KOH was neutralized with 1.0 ml of glacial acetic acid, and the resulting mixture was evaporated to dryness in a rotary evaporator.

EXAMPLE 3

Following preparation of the mixture of example 2, column chromatography was carried out to separate the various constituents. Gangliosides and long chain neutral glycosphingolipids were desalted via reverse phase liquid chromatography (RPLC), on a small Bond Elute $C_{18}$ cartridge, in accordance with Williams, et al., J. Neurochem. 35:266–269 (1980), incorporated by reference in its entirety, while lipids were eluted from the column with 20 ml of C:M (2:1), and 10 additional mls of CH3OH. Pooled eluates were evaporated to dryness, and then resolubilized in 1.0 ml of $CH_3OH$.

The neutral glycosphingolipids and gangliosides were separated from each other via ion exchange chromatography on a DEAE-Sephadex-A-25 column converted to acetate form, in accordance with Ledeen, et al., Meth. Enzymol. 83: 139–191 (1982), incorporated by reference herein, but explained briefly. In short, the resins were batch washed, three times, in 5 volumes of C:M:4M sodium acetate (30:60:8, v/v/v), and the resulting suspension was allowed to stand for at least 12 hours. Any resulting supernatant was discarded, and the resin was again batch washed three times, but this time with 5 volumes of C:M:$H_2O$, (30:60:8 v/v/v). Washed resin was then poured into 0.6 cm inner diameter glass columns, fitted with sand-overlayered glass wool retainers. Each sample was loaded on an individual column, in a minimal volume of methanol. Elution followed. The neutral glycolipids were eluted, in approximately 5 column volumes of methanol, while gangliosides eluted off the column with five column volumes of 0.5M ammonium acetate in methanol.

Ganglioside fractions were diluted with $H_2O$, desalted following Williams, et al., supra, and evaporated to dryness. Total gangliosides were then dissolved in 5.0 ml of C:M(1:1), and stored at –40° C. to prevent evaporation.

EXAMPLE 4

Following the separation of total gangliosides, experiments were carried out to both qualitate and quantitate the product. To do this, an aliquot of each total ganglioside fraction (about 1.0 g wet weight for each) was applied with a TLC spotter to glass backed HPTLC plates (10×20 cm). The gangliosides were chromatographed in a mixture of chloroform/methanol/25% $CaCl_2$ (50:40:10 v/v/v). The mobile phase was allowed to travel to within 1 cm of the top of the plate. The plates were air dried for at least 10 minutes, and then sprayed with resorcinol-HCl reagent. These were then covered with a clean glass plate, and heated in an oven at 110° C., for 7–10 minutes, in accordance with Svennerholm, Eur. J. Biochem. 79:11–21 (1957), incorporated by reference herein.

To establish standards, commercially available gangliosides were chromatographed, simultaneously, for GM1, GM2, GM3, GD1a, GT1b, and GQ1b, all on HPTLC plates.

The profiles were digitized on a Millipore Visage image analysis system, and individual species were quantitated by scanning densitometry, followed by normalization with a Kodak 21 step gray scale wedge. Ganglioside GM1, GM2 and GM3, and sialic acid standards were used to generate densitometry standard curves for quantitation of individual ganglioside species. Ganglioside levels were expressed as ug of ganglioside sialic acid per 100 mg lipid free dry weight (i.e., total remaining dry weight of the original 1 gm sample). Any significant differences between affected and control lambs, at each time point, were determined by two sample t test at the $p<0.05$ level. Poisson correlation coefficients were calculated to determine strength of any linear relationship between individual ganglioside species and disease progression (days of age). Development trends in ganglioside profiles between affected and control lambs were examined by multiple regression.

Results are tabulated in the following tables 1–3. The load of ganglioside-bound sialic acid in affected lambs increased from 2x to 3.2x to 5x the amount in normal lambs over tile three data points (1 day, 120 days, 170 days). Totals ranged from 10.8 μmol (1 day) to 16.6 μmol (120 days), for the affected lambs. For controls, the range was from 2.19 μmol (1 day) to 6.01 μmol. These values are for cerebral cortex samples. With respect to cerebellum cortex samples, the levels in affected lambs at 120 and 170 days were substantially greater than the controls, although the total amount was less than for the affected lambs cerebra. There is a trend of an increase in levels for the affected lambs up to 120 days in the cerebrum, followed by a leveling off. The levels increase overtime in the cerebella. In contrast, the control lambs show a slight decrease over time.

The profile of gangliosides in the samples is presented in Table 2. Notable is the marked increased in GM1. Table 3 shows the concentrations of individual gangliosides, expressed as ug ganglioside sialic acid per 100 mg lipid-free dry weight.

Several comments must be made regarding these tables. First, table 3 presents two columns for "GM3" because two variants of this material, with different molecular weights, were identified. The second form, which is somewhat heavier than the first form, is "astrocyte associated GM3". This form was not found in the control animals, nor were astrocytes found in any appreciable quantity. In preparing the profile for table 3, however, GM3 amounts were added. Hence, there is but a single column for GM3 in table 3.

Analysis of the data shows that the percentage of GM1 ganglioside bound sialic acid, and the concentration of GM1 ganglioside, was significantly elevated in the cerebrum and cerebellum of affected lambs versus controls, at all ages. Also, the percent of GM1 ganglioside bound sialic acid in both the cerebrum and the cerebellum levelled off after 120 days, as Table 2 shows. The concentration of GM1 ganglioside leveled off after 120 days in the cerebrum, yet increased through 160 days in the cerebellum. In control lambs, GM1 ganglioside concentrations decreased, generally over 170 days.

Other ganglioside species are also assessed. Note that GM3 concentrations were elevated, significantly, at all time points in both cerebra and cerebella of the affected lambs. In normal lambs, GM3 concentration decreased over the 170 days, and was below the detection threshold (0.25 ug sialic acid) in the cerebellum.

GM2 concentrations were significantly elevated in the cerebra of afflicted animals toward the 170 day mark; however, there weren't significant differences in concentrations of GM2 vis-a-vis the two groups of animals at days 1 and 120; in contrast, the levels of GM2 in cerebella were elevated at each time point, although the differences were not significant at $P<0.05$. For normal lambs, there was a decreasing trend from day 1 through day 170.

There were also significant elevations in levels of GQ1b in the cerebra of afflicted lambs at each time point; however, as table 3 shows, the concentration did decrease slightly with age, during disease progression, at a rate similar to the GQ1b levels in normal cerebra. In contrast, the GQ1b levels in cerebella of affected lambs were similar to or slightly less at all time points versus control lambs, with the concentration in the cerebellum remaining fairly constant at all ages.

As to GD1a, the concentrations were not significantly elevated in affected versus control lambs, and the percentage of total ganglioside bound sialic acid represented by GD1a decreased in both types of samples during disease progression. In contrast, GD1b levels were elevated at days 120 and 170 in the cerebrum, and slightly, though not significantly elevated, in the cerebellum, at all ages. With respect to afflicted lambs, the levels of GD1b were similar at day 1 and day 120, with a slight decrease at day 170. In contrast, levels for normal lambs decreased from day 1 to day 170 (cerebra), while staying relatively constant in the cerebellum over the same period.

Trisialoganglioside levels ("GT1b"), were significantly elevated at 170 days in the cerebra of affected lambs, while cerebellum levels were slightly less than control lambs throughout the period. Levels of GT1b gangliosides did, however, remain fairly constant in all of the lambs.

The foregoing examples describe a methodology by which surprisingly high yields of lipid containing molecules can be obtained. In particular, glycolipid molecules such as the gangliosides, especially GM1. It has been found that these molecules occur in exceptional high concentration in the neural tissues of animals which suffer from "GM1 gangliosides". Neural tissue" as used herein is to be interpreted broadly, and encompasses all portions of the brain, including the cerebrum, cerebellum, medulla, etc. Also included is spinal cord tissue, as well as all other neural tissues.

The extraction of the lipid containing molecules can be accomplished via the use of various extracting agents. These agents can be single substances, or mixtures of several, depending upon the nature of the lipid containing molecules of interest. Examples of some of the solvents which can be used are water, chloroform, methanol, and combinations of these. Any of the other standard lipid extraction solvents many also be used. For example, as described, supra, an extraction agent containing chloroform and methanol in a 2:1 ratio may be used, followed by $CH_3OH$ containing KOH. In another embodiment, a solvent containing chloroform, methanol and water may be used. This can be followed with a wash of ammonium acetate, when the desired materials are gangliosides.

As indicated, supra, the source of the lipid containing molecules is neural tissue from GM1 gangliosidosis afflicted animals. This condition affects ovine animals, e.g., sheep, and is a fatal condition. Generally, lambs afflicted with the condition live long enough to produce gametes, but do not live long enough to reproduce sexually. GM1 gangliosidosis is a recessive trait, and is carried by animals which are otherwise healthy but are heterozygous for the gene. The usual rules of Mendelian genetics apply, and one thus expects that in a mating of two heterozygous animals, 25% of the offspring will have the condition, while another 50% of the population, will carry the condition, but will not suffer from the disease. Thus, the means for producing the necessary animals are available; however, to facilitate the availability of such animals, heterozygous semen will be made available at a public depository for use in the practice of the invention. Such semen is used with, e.g., a normal female to produce a population of offspring of which 50% are carriers of the gene. These offspring may then be crossbred to produce a population of animals which can then be used. The gestation period for ovine animals is relatively short, and the amount of time to sexual maturity is such that the length of time necessary to secure suitable tissue is not out of line with other similar methods of breeding animals.

Other features of the invention will be clear to the skilled artisan and need not be reiterated here.

It will be understood that the specification and examples are illustrative but not limitative of the present invention and that other embodiments within the spirit and scope of the invention will suggest themselves to those skilled in the art.

TABLE 1

Total ganglioside concentration in ovine GM1 gangliosidosis[a]
μmol ganglioside sialic acid/gm wet weight (mean ± sd)

|  |  | Affected | Control |
|---|---|---|---|
| Cerebrum (cortex)[b] |  |  |  |
| Age(days) | 1 | *11.27 ± 0.41 | 5.82 ± 0.26 |
|  | 120 | *14.25 ± 2.54 | 4.41 ± 0.22 |
|  | 170 | *12.97 ± 2.24 | 2.62 ± 0.44 |
| Cerebellum (cortex)[c] |  |  |  |
| Age(days) | 1 | 2.56 ± 0.21 | 1.91 ± 0.47 |
|  | 120 | *5.35 ± 0.26 | 1.83 ± 0.00 |
|  | 170 | *7.81 ± 0.45 | 1.66 ± 0.47 |

[a]Gangliosides were isolated from the indicated regions, purified and analyzed by HPTLC in conjunction with scanning densitometry.
[b]Total ganglioside sialic acid values for the cerebrum are mean values from 3 affected and 3 control lambs at each time-point.
[c]Total ganglioside sialic acid values for the cerebellum are mean values from 2 affected and 2 control lambs at each time-point.
*Significant difference between affected and control lambs, $p < 0.05$.

TABLE 2

Ganglioside distribution patterns in ovine GM1 gangliosidosis

|  |  | Percent of ganglioside sialic acid (mean ± sd)[a] | | | | |
|---|---|---|---|---|---|---|
|  | Status | GM3 | GM3 | GM2 | GM1 | GD3 |
| Cerebrum (cortex)[b] |  |  |  |  |  |  |
| Day 1 | affected | 0.18 ± 0.03 | 0.70 ± 0.11 | 2.13 ± 0.35 | 47.11 ± 1.42 | 1.32 ± 0.06 |
|  | control | ND[d] | 0.71 ± 0.24 | 2.41 ± 1.14 | 17.09 ± 2.26 | 2.58 ± 0.86 |
| Day 120 | affected | 0.24 ± 0.22 | 0.61 ± 0.12 | 1.20 ± 0.59 | 69.37 ± 1.85 | ND[d] |
|  | control | ND[d] | 0.66 ± 0.13 | 2.41 ± 0.64 | 16.55 ± 0.98 | 2.92 ± 0.42 |
| Day 170 | affected | 0.44 ± 0.18 | 0.84 ± 0.21 | 1.41 ± 0.28 | 71.48 ± 3.67 | ND[d] |

TABLE 2-continued

Ganglioside distribution patterns in ovine GM1 gangliosidosis

|  |  |  |  |  |  |  |
|---|---|---|---|---|---|---|
|  | control | ND[d] | 0.67 ± 0.08 | 1.95 ± 0.51 | 19.83 ± 2.57 | 2.65 ± 0.56 |
| Cerebellum (cortex)[c] |  |  |  |  |  |  |
| Day 1 | affected | 0.28 ± 0.03 | 0.68 ± 0.01 | 2.19 ± 0.21 | 49.62 ± 1.80 | 1.96 ± 0.42 |
|  | control | ND[d] | ND[d] | 2.33 ± 1.18 | 2.81 ± 1.70 | 6.51 ± 1.19 |
| Day 120 | affected | 0.27 ± 0.01 | 0.72 ± 0.01 | 3.00 ± 1.41 | 77.84 ± 0.57 | ND[d] |
|  | control | ND[d] | ND[d] | 1.27 ± 0.33 | 2.07 ± 0.06 | 7.83 ± 0.86 |
| Day 170 | affected | 0.19 ± 0.04 | 1.00 ± 0.06 | 5.59 ± 4.64 | 79.85 ± 5.40 | ND[d] |
|  | control | ND[d] | ND[d] | 0.78 ± 0.06 | 1.04 ± 0.23 | 6.31 ± 0.40 |

| | Percent of ganglioside sialic acid (mean ± sd)[a] | | | |
|---|---|---|---|---|
| | GD1a | GD1b | GT1b | GQ1b |
| Cerebrum (cortex)[b] | | | | |
| Day 1 | 29.95 ± 1.67 | 7.95 ± 0.33 | 8.74 ± 0.83 | 1.92 ± 0.26 |
|  | 52.26 ± 2.53 | 10.39 ± 0.75 | 13.17 ± 1.28 | 1.99 ± 0.17 |
| Day 120 | 14.30 ± 1.07 | 6.39 ± 1.11 | 6.28 ± 1.83 | 1.60 ± 0.39 |
|  | 50.96 ± 3.36 | 9.97 ± 0.37 | 14.44 ± 2.18 | 2.11 ± 0.58 |
| Day 170 | 12.41 ± 3.91 | 5.63 ± 0.73 | 6.18 ± 1.25 | 1.61 ± 0.29 |
|  | 49.10 ± 3.21 | 8.62 ± 0.60 | 15.86 ± 0.33 | 1.32 ± 0.12 |
| Cerebellum (cortex)[c] | | | | |
| Day 1 | 12.72 ± 0.16 | 10.64 ± 3.25 | 16.83 ± 3.38 | 3.66 ± 0.81 |
|  | 20.29 ± 0.97 | 7.97 ± 2.58 | 42.00 ± 3.14 | 8.98 ± 0.98 |
| Day 120 | 3.09 ± 0.41 | 4.99 ± 0.28 | 7.38 ± 0.27 | 2.23 ± 0.46 |
|  | 24.21 ± 3.32 | 9.35 ± 0.00 | 37.42 ± 3.15 | 7.83 ± 0.42 |
| Day 170 | 2.86 ± 0.01 | 3.40 ± 0.12 | 4.77 ± 0.07 | 1.40 ± 0.33 |
|  | 19.17 ± 0.33 | 8.90 ± 0.56 | 42.47 ± 3.35 | 10.54 ± 0.66 |

[a]Ganglioside fractions were separated by HPTLC and analyzed by scanning densitometry. Percent of total ganglioside sialic acid for individual ganglioside species is expressed as a mean ± standard deviation
[b]Percent distribution of individual ganglioside species for the cerebrum was generated from 3 affected and 3 control lambs at each time-point.
[c]Percent distribution of individual ganglioside species for the cerebellum was generated from 2 affected and 2 control lambs at each time-point.
[d]ND = not detected; <0.25 μg sialic acid

TABLE 3

Ganglioside profiles in ovine GM1 gangliosidosis

| | | μg sialic acid/100 mg lipid-free dry weight (mean ± sd)[a] | | | |
|---|---|---|---|---|---|
| | | GM3 | GM2 | GM1 | GD1a |
| Cerebrum (cortex)[b] | | | | | |
| Day 1 | affected | 31.63 ± 2.00* | 76.49 ± 9.47 | 1702.70 ± 38.83* | 1085.46 ± 112.01 |
|  | control | 14.62 ± 3.72 | 45.97 ± 13.98 | 363.47 ± 137.31 | 932.75 ± 74.67 |
| Day 120 | affected | 30.37 ± 6.33* | 38.45 ± 16.10 | 2752.49 ± 603.57* | 570.22 ± 144.70 |
|  | control | 8.99 ± 0.64 | 31.77 ± 7.61 | 216.23 ± 8.98 | 552.66 ± 108.00 |
| Day 170 | affected | 40.29 ± 13.14* | 41.39 ± 9.91* | 2132.79 ± 473.27* | 381.82 ± 143.44 |
|  | control | 4.45 ± 1.47 | 13.17 ± 5.77 | 129.35 ± 22.89 | 321.86 ± 60.42 |
| Cerebellum (cortex)[c] | | | | | |
| Day 1 | affected | 7.28 ± 0.27* | 16.67 ± 2.98 | 376.31 ± 17.08* | 96.59 ± 9.08 |
|  | control | ND[d] | 9.73 ± 2.73 | 11.58 ± 4.50 | 91.12 ± 26.82 |
| Day 120 | affected | 15.76 ± 0.75* | 46.95 ± 19.92 | 1233.99 ± 68.78* | 49.16 ± 8.94 |
|  | control | ND[d] | 5.41 ± 1.45 | 8.82 ± 0.27 | 103.38 ± 13.97 |
| Day 170 | affected | 26.35 ± 0.00* | 73.55 ± 25.41 | 1851.01 ± 231.13* | 66.22 ± 4.07 |
|  | control | ND[d] | 3.71 ± 0.43 | 3.97 ± 0.80 | 94.60 ± 8.83 |

| | | μg sialic acid/100 mg lipid-free dry weight (mean ± sd)[a] | | |
|---|---|---|---|---|
| | | GD1b | GT1b | GQ1b |
| Cerebrum (cortex)[b] | | | | |
| Day 1 | | 263.93 ± 14.16 | 316.45 ± 35.79 | 69.97 ± 13.15* |

TABLE 3-continued

| Ganglioside profiles in ovine GM1 gangliosidosis | | | |
|---|---|---|---|
| | 204.94 ± 85.24 | 270.95 ± 51.16 | 34.90 ± 4.36 |
| Day 120 | 273.08 ± 33.33* | 238.87 ± 19.98 | 61.51 ± 4.69* |
| | 125.53 ± 15.66 | 188.10 ± 21.08 | 27.41 ± 6.69 |
| Day 170 | 218.40 ± 61.89* | 179.23 ± 4.49* | 46.96 ± 5.24* |
| | 58.87 ± 12.70 | 103.79 ± 17.63 | 8.71 ± 2.16 |
| Cerebellum (cortex)[c] | | | |
| Day 1 | 79.73 ± 18.02 | 128.89 ± 36.05 | 28.03 ± 8.33 |
| | 34.15 ± 2.68 | 189.32 ± 60.66 | 40.96 ± 14.78 |
| Day 120 | 79.01 ± 0.61 | 117.10 ± 9.89 | 35.46 ± 8.94 |
| | 39.94 ± 0.05 | 159.87 ± 13.76 | 33.43 ± 1.87 |
| Day 170 | 78.43 ± 1.69 | 110.39 ± 7.86 | 32.10 ± 5.69 |
| | 40.66 ± 3.75 | 182.01 ± 38.55 | 40.17 ± 9.69 |

[a]Ganglioside fractions were separated by HPTLC and analyzed by scanning densitometry. Concentrations of individual ganglioside species are expressed as µg sialic acid per 100 mg lipid free dry weight. Values given are the mean ± standard deviation.
[b]Concentrations of individual ganglioside species for the cerebrum were generated from 3 affected and 3 control lambs at each time-point.
[c]Concentrations of individual ganglioside species for the cerebellum were generated from 2 affected and 2 control lambs at each time-point.
[d]ND = not detected; <0.25 µg sialic acid
*Significant differences between affected and control lambs at $p < 0.05$ using a two sample t-test.

I claim:

1. Process for obtaining a ganglioside lipid molecule comprising: contacting a sample of neural tissue obtained from an ovine animal afflicted with GM1 gangliosidosis with an extracting agent, under conditions favoring extraction of ganglioside lipid molecules from said neural tissue, and removing extracted ganglioside lipid molecules from said extracting agent, wherein the amount of ganglioside lipid molecules obtained are enhanced as compared to the amount of ganglioside lipid molecules obtained from non-afflicted ovine animals.

2. The process of claim 1, wherein said ganglioside is a monosialoganglioside.

3. The process of claim 1, wherein said neural tissue is brain tissue.

4. The process of claim 1, wherein said neural tissue is spinal cord tissue.

5. The process of claim 1, further comprising homogenizing said neural tissue prior to contacting with said extracting agent.

6. The process of claim 5, comprising homogenizing said neural tissue in water.

7. The process of claim 1, wherein said extracting agent comprises chloroform.

8. The process of claim 1, wherein said extracting agent comprises methanol.

9. The process of claim 1, wherein said extracting agent comprises water.

10. The process of claim 1, wherein said extracting agent comprises chloroform, methanol, and water.

* * * * *